(12) United States Patent
Liu et al.

(10) Patent No.: US 10,858,307 B2
(45) Date of Patent: Dec. 8, 2020

(54) COMPOSITIONS AND METHODS FOR TREATING LIVER CANCER

(71) Applicant: Golden Biotechnology Corporation, Jersey City, NJ (US)

(72) Inventors: Sheng-Yung Liu, New Taipei (TW); Chih-Ming Chen, New Taipei (TW)

(73) Assignee: Golden Biotechnology Corporation, Jersey City, NJ (US)

(*) Notice: Subject to any disclaimer, the term of this patent is extended or adjusted under 35 U.S.C. 154(b) by 124 days.

(21) Appl. No.: 15/999,358

(22) PCT Filed: Feb. 16, 2017

(86) PCT No.: PCT/US2017/018236
§ 371 (c)(1),
(2) Date: Aug. 17, 2018

(87) PCT Pub. No.: WO2017/143106
PCT Pub. Date: Aug. 24, 2017

(65) Prior Publication Data
US 2019/0112258 A1    Apr. 18, 2019

Related U.S. Application Data

(60) Provisional application No. 62/296,097, filed on Feb. 17, 2016.

(51) Int. Cl.
| | | |
|---|---|---|
| *C07C 225/00* | (2006.01) | |
| *C07C 225/20* | (2006.01) | |
| *C07D 333/20* | (2006.01) | |
| *C07D 213/36* | (2006.01) | |
| *C07C 49/557* | (2006.01) | |
| *C07D 209/16* | (2006.01) | |
| *C07C 49/543* | (2006.01) | |
| *A61K 31/12* | (2006.01) | |
| *A61P 35/00* | (2006.01) | |
| *C07D 209/14* | (2006.01) | |

(52) U.S. Cl.
CPC ............ *C07C 225/20* (2013.01); *A61K 31/12* (2013.01); *A61P 35/00* (2018.01); *C07C 49/543* (2013.01); *C07C 49/557* (2013.01); *C07D 209/14* (2013.01); *C07D 209/16* (2013.01); *C07D 213/36* (2013.01); *C07D 333/20* (2013.01); *C07C 2601/16* (2017.05)

(58) Field of Classification Search
CPC ..................................................... C07C 225/00
See application file for complete search history.

(56) References Cited

U.S. PATENT DOCUMENTS

2015/0018567 A1* 1/2015 Liu .................. C07C 49/753
549/323

FOREIGN PATENT DOCUMENTS

| EP | 2233463 A1 * | 9/2010 | ............. A61K 36/07 |
| EP | 2233463 A1 | 9/2010 | |

OTHER PUBLICATIONS

Han, H. "Targeted Prodrug Design to Optimize Drug Delivery." AAPS Pharmsci. (2000), vol. 2 (1) article 6, pp. 1-11. (Year: 2000).*
Ettmayer, P., et al. "Lessons Learned from Marketed and Investigational Prodrugs." J. Med. Chem. (2004) 47(10), pp. 2393-2404. (Year: 2004).*
Testa, B. "Prodrug research: futile or fertile?" Biochem. Pharm. (2004) 68, pp. 2097-2106. (Year: 2004).*

* cited by examiner

*Primary Examiner* — John S Kenyon
(74) *Attorney, Agent, or Firm* — Chang-Hsing Liang

(57) ABSTRACT

Provided herein are compositions and methods of treating liver cancer by novel anticancer agents.

18 Claims, 3 Drawing Sheets

COMPOSITIONS AND METHODS FOR TREATING LIVER CANCER

BACKGROUND OF THE INVENTION

Liver cancer, also known as hepatic cancer, is a cancer that originates in the liver. Primary liver cancer is globally the sixth most frequent cancer, and the second leading cause of cancer death. The most frequent liver cancer, accounting for approximately 75% of all primary liver cancers, is hepatocellular carcinoma (HCC) (also named hepatoma, which is a misnomer because adenomas are usually benign). HCC is a cancer formed by liver cells, known as hepatocytes that become malignant. Hepatocellular carcinoma accounts for more than half million deaths annually worldwide.

SUMMARY OF THE INVENTION

In one aspect, there are provided a compound of formula I:

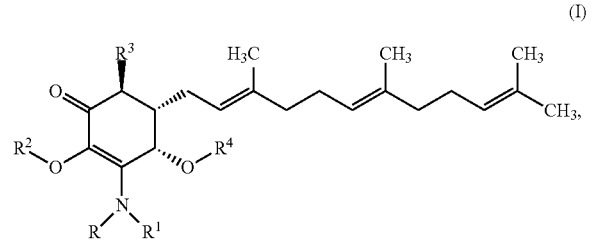

(I)

or a pharmaceutically acceptable salt, metabolite, solvate or prodrug thereof,
wherein each of each of R, and $R^1$ independently is a hydrogen, C(=O)OR$_5$, C(=O)R$_5$, C(=O)NR$_5$R$_6$, or $C_1$-$C_8$alkyl optionally substituted with one or more halogen, NR$_5$R$_6$, OR$_5$, aryl or heteroaryl;
$R^2$ is a hydrogen, C(=O)OR$_5$, C(=O)R$_5$, C(=O)NR$_5$R$_6$, or $C_1$-$C_8$alkyl optionally substituted with one or more halogen, aryl or heteroaryl,
$R^3$ is a hydrogen, optionally substituted methyl or $(CH_2)_m$—$CH_3$,
$R^4$ is H, C(=O)OR$_5$, C(=O)R$_5$, C(=O)NR$_5$R$_6$, $C_1$-$C_8$alkyl, $C_2$-$C_8$alkenyl, $C_2$-$C_8$alkynyl, wherein the $C_1$-$C_5$alkyl, $C_2$-$C_8$alkenyl, $C_2$-$C_8$alkynyl, are optionally substituted with one or more substituents selected from NR$_5$R$_6$, OR$_5$, OC(=O)R$_7$, C(=O)OR$_5$, C(=O)R$_5$, C(=O)NR$_5$R$_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of R$_5$ and R$_6$ is independently H or $C_1$-$C_5$alkyl;
R$_7$ is a $C_1$-$C_5$alkyl, OR$_5$ or NR$_5$R$_6$.

In one aspect, there are provided a compound of formula Ia:

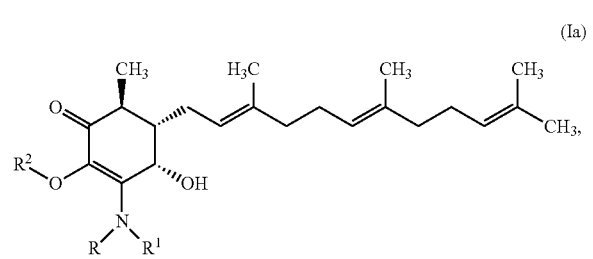

(Ia)

or a pharmaceutically acceptable salt, metabolite, solvate or prodrug thereof, wherein each of each of R, and $R^1$ independently is a hydrogen, C(=O)OR$_5$, C(=O)R$_5$, C(=O)NR$_5$R$_6$, or $C_1$-$C_8$alkyl optionally substituted with one or more halogen, NR$_5$R$_6$, OR$_5$, aryl or heteroaryl;
$R^2$ is a hydrogen, C(=O)OR$_5$, C(=O)R$_5$, C(=O)NR$_5$R$_6$, or $C_1$-$C_8$alkyl optionally substituted with one or more halogen, aryl or heteroaryl, and each of R$_5$ and R$_6$ is independently H or $C_1$-$C_8$alkyl.

In another aspect, there are provided methods for treating or reducing the risk of liver cancer in a subject comprising administering to said subject a therapeutically effective amount of an anti-cancer agent having the structure:

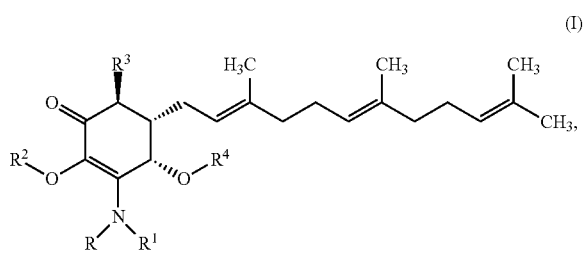

(I)

or a pharmaceutically acceptable salt, metabolite, solvate or prodrug thereof,
wherein each of each of R, and $R^1$ independently is a hydrogen, C(=O)OR$_5$, C(=O)R$_5$, C(=O)NR$_5$R$_6$, or $C_1$-$C_8$alkyl optionally substituted with one or more halogen, NR$_5$R$_6$, OR$_5$, aryl or heteroaryl;
$R^2$ is a hydrogen, C(=O)OR$_5$, C(=O)R$_5$, C(=O)NR$_5$R$_6$, or $C_1$-$C_8$alkyl optionally substituted with one or more halogen, NR$_5$R$_6$, OR$_5$, $C_6$-$C_{10}$aryl or $C_4$-$C_{10}$heteroaryl,
$R^3$ is a hydrogen, optionally substituted methyl or $(CH_2)_m$—$CH_3$,
$R^4$ is H, C(=O)OR$_5$, C(=O)R$_5$, C(=O)NR$_5$R$_6$, $C_1$-$C_8$alkyl, $C_2$-$C_8$alkenyl, $C_2$-$C_8$alkynyl, wherein the $C_1$-$C_8$alkyl, $C_2$-$C_8$alkenyl, $C_2$-$C_8$alkynyl, are optionally substituted with one or more substituents selected from NR$_5$R$_6$, OR$_5$, OC(=O)R$_7$, C(=O)OR$_5$, C(=O)R$_5$, C(=O)NR$_5$R$_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;
each of R$_5$ and R$_6$ is independently H or $C_1$-$C_8$alkyl; and
R$_7$ is a $C_1$-$C_8$alkyl, OR$_5$ or NR$_5$R$_6$.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
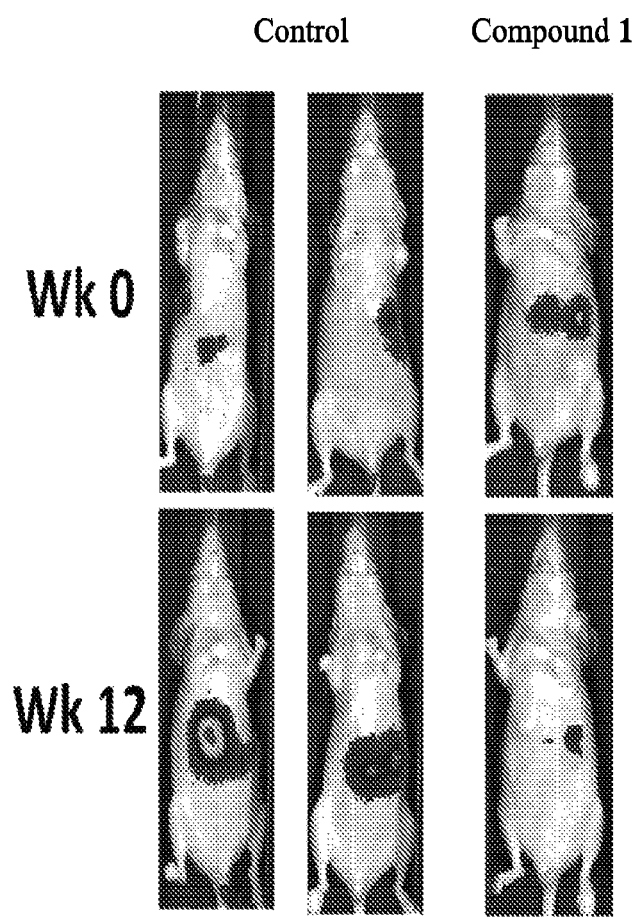
FIG. 1 illustrates the tumor size test results of THP-1 xenograft mice treated with and without the exemplary invention compound.

The present invention provides novel anticancer agents and methods of treating liver cancer therefrom. For example, the following exemplary anticancer compounds 1-11 were prepared and test for anticancer activities over liver cancer cells. The exemplary anticancer agents are analogs of 4-hydroxy-2,3-dimethoxy-6-methyl-5-(3,7,11-trimethyldodeca-2,6,10-trienyl)cyclohex-2-enone (Compound S). However, it was found unexpectedly that those 3-amino derivatives possess superb inhibition, compared to their 3-hydroxyl analog, 4-hydroxy-2,3-dimethoxy-6-methyl-5-(3,7,11-trimethyldodeca-2,6,10-trienyl)cyclohex-2-enone, against liver cancer cells with some of them 10 to 20 folds better. Subsequent in vivo study confirms these compounds are good candidate for liver cancer treatment.

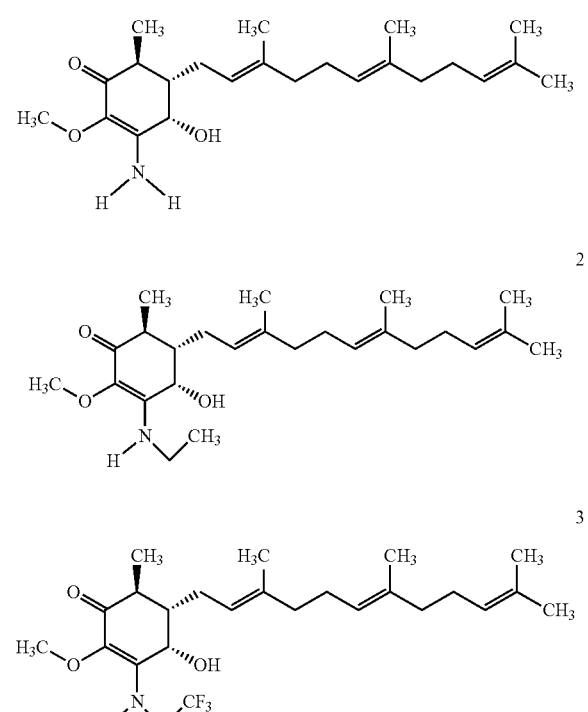

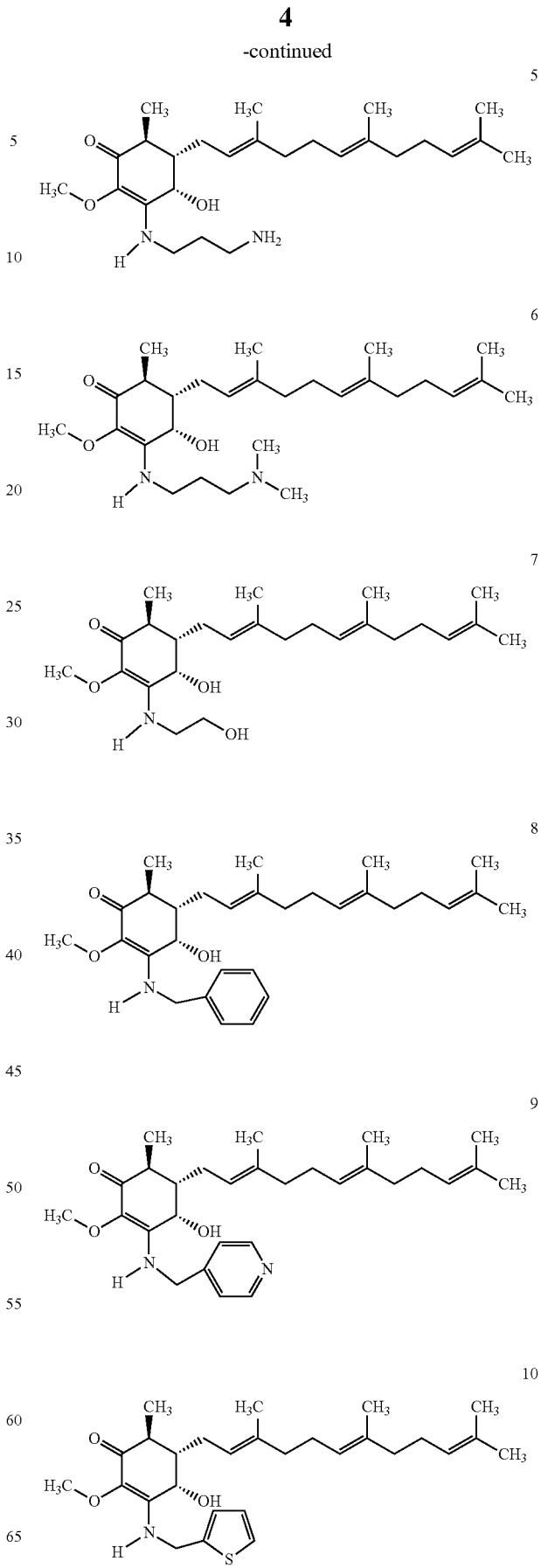

-continued (11)

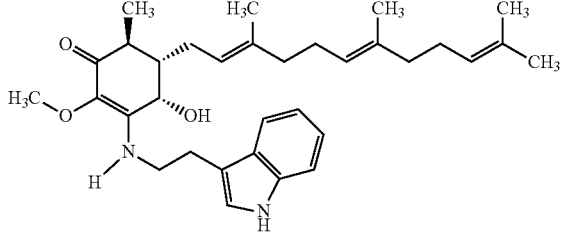

In some embodiments, there are provided herein a compound of formula I

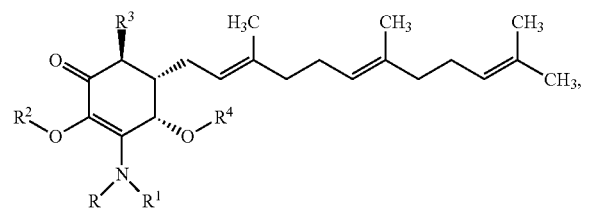

(I)

or a pharmaceutically acceptable salt, metabolite, solvate or prodrug thereof,
wherein each of R, and $R^1$ independently is a hydrogen, $C(=O)OR_5$, $C(=O)R_5$, $C(=O)NR_5R_6$, or $C_1$-$C_5$alkyl optionally substituted with one or more halogen, $NR_5R_6$, $OR_5$, aryl or heteroaryl;

$R^2$ is a hydrogen, $C(=O)OR_5$, $C(=O)R_5$, $C(=O)NR_5R_6$, or $C_1$-$C_8$alkyl optionally substituted with one or more halogen, aryl or heteroaryl, $R^3$ is a hydrogen, optionally substituted methyl or $(CH_2)_m$—$CH_3$, $R^4$ is H, $C(=O)OR_5$, $C(=O)R_5$, $C(=O)NR_5R_6$, $C_1$-$C_8$alkyl, $C_2$-$C_8$alkenyl, $C_2$-$C_8$alkynyl, wherein the $C_1$-$C_8$alkyl, $C_2$-$C_8$alkenyl, $C_2$-$C_8$alkynyl, are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently H or $C_1$-$C_8$alkyl; and $R_7$ is a $C_1$-$C_5$alkyl, $OR_5$ or $NR_5R_6$.

In certain embodiments, R is hydrogen (H), $C_1$-$C_8$alkyl, or $C_1$-$C_8$alkyl substituted with one or more halogen, $NR_5R_6$, $OR_5$, $C_6$-$C_{10}$aryl or $C_4$-$C_{10}$heteroaryl. In certain embodiments, R is a hydrogen (H), methyl, ethyl, propyl, butyl, pentyl, hexyl, or the like, optionally substituted with one or more halogen, $NR_5R_6$, $OR_5$, $C_6$-$C_{10}$aryl or $C_4$-$C_{10}$heteroaryl. In certain embodiments, R is H, or $C_1$-$C_5$alkyl. In certain embodiments, R is hydrogen, methyl, ethyl, propyl, butyl, pentyl, or hexyl. In certain embodiments, R is a hydrogen, $C(=O)OR_5$, $C(=O)R_5$, or $C(=O)NR_5R_6$. In certain embodiments, R is H, $C_1$-$C_8$alkyl, $C(=O)OR_5$, $C(=O)R_5$, or $C(=O)NR_5R_6$. In certain embodiments, R is H, or $C(=O)R_5$. In certain embodiments, R is H, $C(=O)C_3H_8$, $C(=O)C_2H_5$, or $C(=O)CH_3$. In certain embodiments, R is H, $C_1$-$C_8$alkyl, or $C_1$-$C_8$alkyl substituted with one or more $NR_5R_6$, or $C_4$-$C_{10}$heteroaryl.

In certain embodiments, $R^1$ is hydrogen (H). In certain embodiments, $R^1$ is hydrogen, $C_1$-$C_8$alkyl, or $C_1$-$C_8$alkyl substituted with one or more halogen, $NR_5R_6$, $OR_5$, $C_6$-$C_{10}$aryl or $C_4$-$C_{10}$heteroaryl. In certain embodiments, $C_6$-$C_{10}$aryl is phenyl. In certain embodiments, $C_4$-$C_{10}$heteroaryl is pyridyl, thiophenyl, or indolyl. In certain embodiments, $R^1$ is hydrogen, or $C_1$-$C_8$alkyl. In certain embodiments, $R^1$ is H, $C_1$-$C_8$alkyl, or $C_1$-$C_8$alkyl substituted with one or more $NR_5R_6$, or $C_4$-$C_{10}$heteroaryl. In certain embodiments, $R^1$ is a hydrogen (H), methyl, ethyl, propyl, butyl, pentyl, hexyl, or the like, optionally substituted with one or more halogen, $NR_5R_6$, $OR_5$, $C_6$-$C_{10}$aryl or $C_4$-$C_{10}$heteroaryl. In certain embodiments, $R^1$ is hydrogen, methyl, ethyl, propyl, butyl, optionally substituted with $NR_5R_6$, $OR_5$, $C_6$-$C_{10}$aryl or $C_4$-$C_{10}$heteroaryl. In certain embodiments, $R^1$ is hydrogen, methyl, methyl substituted with $C_4$-$C_{10}$heteroaryl such as thiophenyl, ethyl substituted with $OR_5$ such as OH, ethyl substituted with $C_4$-$C_{10}$heteroaryl such as indolyl, propyl substituted with $NR_5R_6$ such as $NH_2$. In certain embodiments, $R^1$ is hydrogen, methyl, methyl substituted with $C_4$-$C_{10}$heteroaryl such as thiophenyl, or propyl substituted with $NR_5R_6$ such as $NH_2$.

In some embodiments, R is hydrogen, or $C(=O)R_5$; and $R^1$ is hydrogen, $C_1$-$C_8$alkyl, or $C_1$-$C_8$alkyl substituted with one or more halogen, $NR_5R_6$, $OR_5$, $C_6$-$C_{10}$aryl or $C_4$-$C_{10}$heteroaryl. In certain embodiments, R is $C_1$-$C_8$alkyl and $R^1$ is $C_1$-$C_8$alkyl. In certain embodiments, R is hydrogen, and $R^1$ is hydrogen, $C_1$-$C_8$alkyl, or $C_1$-$C_8$alkyl substituted with one or more halogen, $NR_5R_6$, $OR_5$, $C_6$-$C_{10}$aryl or $C_4$-$C_{10}$heteroaryl. In particular, R is hydrogen, and $R^1$ is hydrogen, methyl, ethyl, propyl, butyl, optionally substituted with $NR_5R_6$, $OR_5$, $C_6$-$C_{10}$aryl or $C_4$-$C_{10}$heteroaryl. In certain embodiments, R is hydrogen, and $R^1$ is hydrogen, methyl, methyl substituted with $C_4$-$C_{10}$heteroaryl such as thiophenyl, ethyl substituted with $OR_5$ such as OH, ethyl substituted with $C_4$-$C_{10}$heteroaryl such as indolyl, or propyl substituted with $NR_5R_6$ such as $NH_2$. In certain embodiments, R is hydrogen or methyl, and $R^1$ is hydrogen, methyl, methyl substituted with $C_4$-$C_{10}$heteroaryl such as thiophenyl, or propyl substituted with $NR_5R_6$ such as $NH_2$.

In some embodiments, $R^2$ is methyl, ethyl, propyl, butyl, pentyl, hexyl, or the like. In some embodiments, $R^2$ is $C(=O)OR_5$, $C(=O)R_5$, $C(=O)NR_5R_6$. In some embodiments, $R^2$ is $C(=O)C_3H_7$, $C(=O)C_2H_5$, $C(=O)CH_3$, $C(=O)OC_3H_7$, $C(=O)OC_2H_5$, $C(=O)OCH_3$, $C(=O)NHC_3H_7$, $C(=O)NHC_2H_5$, or $C(=O)NHCH_3$. In certain embodiments, $R^2$ is methyl.

In some embodiments, $R^3$ is hydrogen, methyl, ethyl, propyl, butyl, pentyl, hexyl, or the like. In certain embodiments, $R^3$ is methyl.

In some embodiments, $R^4$ is hydrogen (H), $C(=O)OR_5$, $C(=O)R_5$, $C(=O)NR_5R_6$, or $C_1$-$C_8$alkyl. In certain embodiments, $R^4$ is H hydrogen, methyl, ethyl, propyl, butyl, pentyl, hexyl, or the like. In some embodiments, $R^4$ is $C(=O)OR_5$, $C(=O)R_5$, $C(=O)NR_5R_6$. In some embodiments, $R^4$ is $C(=O)C_3H_7$, $C(=O)C_2H_5$, $C(=O)CH_3$, $C(=O)OC_3H_7$, $C(=O)OC_2H_5$, $C(=O)OCH_3$, $C(=O)NHC_3H_7$, $C(=O)NHC_2H_5$, or $C(=O)NHCH_3$. In certain embodiments, $R^4$ is hydrogen.

In some embodiments, there are provided herein a compound of formula Ia

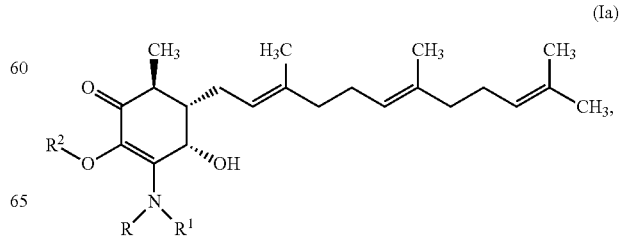

(Ia)

or a pharmaceutically acceptable salt, metabolite, solvate or prodrug thereof, wherein each of each of R, and $R^1$ independently is a hydrogen, C(=O)OR$_5$, C(=O)R$_5$, C(=O)NR$_5$R$_6$, or $C_1$-$C_8$alkyl optionally substituted with one or more halogen, NR$_5$R$_6$, OR$_5$, aryl or heteroaryl;

$R^2$ is a hydrogen, C(=O)OR$_5$, C(=O)R$_5$, C(=O)NR$_5$R$_6$, or $C_1$-$C_8$alkyl optionally substituted with one or more halogen, aryl or heteroaryl; and each of R$_5$ and R$_6$ is independently H or $C_1$-$C_8$alkyl.

In some embodiments, each of R, and $R^1$ independently is a hydrogen, methyl, ethyl, propyl, butyl, pentyl, hexyl, or the like, optionally substituted with one or more halogen, NR$_5$R$_6$, OR$_5$, aryl or heteroaryl. In certain embodiments, R is H, C(=O)OR$_5$, C(=O)R$_5$, C(=O)NR$_5$R$_6$. In certain embodiments, R is H, or C(=O)R$_5$. In certain embodiments, R is H, C(=O)C$_3$H, C(=O)C$_2$H$_5$, or C(=O)CH$_3$. In certain embodiments, $R^1$ is hydrogen. In certain embodiments, R is hydrogen, $C_1$-$C_8$alkyl, $C_1$-$C_8$alkyl substituted with one or more halogen, NR$_5$R$_6$, OR$_5$, aryl or heteroaryl. In certain embodiments, aryl is phenyl. In certain embodiments, heteroaryl is pyridyl, thiophenyl, or indolyl.

In some embodiments, $R^2$ is methyl, ethyl, propyl, butyl, pentyl, hexyl, or the like. In some embodiments, $R^2$ is C(=O)OR$_5$, C(=O)R$_5$, C(=O)NR$_5$R$_6$. In some embodiments, $R^2$ is C(=O)C$_3$H$_7$, C(=O)C$_2$H$_5$, C(=O)CH$_3$, C(=O)OC$_3$H$_7$, C(=O)OC$_2$H$_5$, C(=O)OCH$_3$, C(=O)NHC$_3$H$_7$, C(=O)NHC$_2$H$_5$, or C(=O)NHCH$_3$. In certain embodiments, $R^2$ is methyl.

In certain embodiments provide a compound of formula I

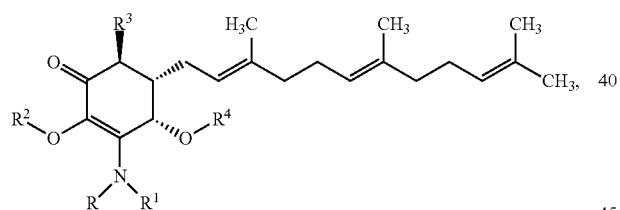

(I)

or a pharmaceutically acceptable salt, metabolite, solvate or prodrug thereof, wherein the compound is selected from the group consisting of

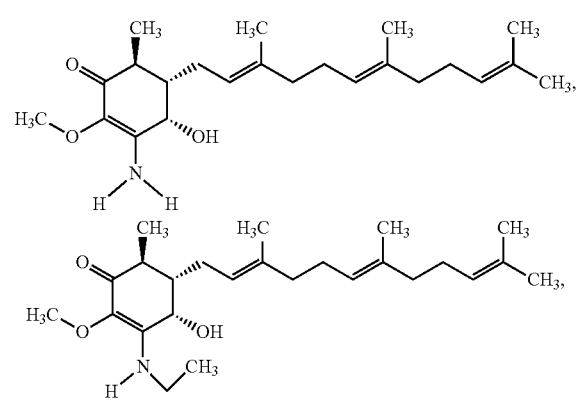

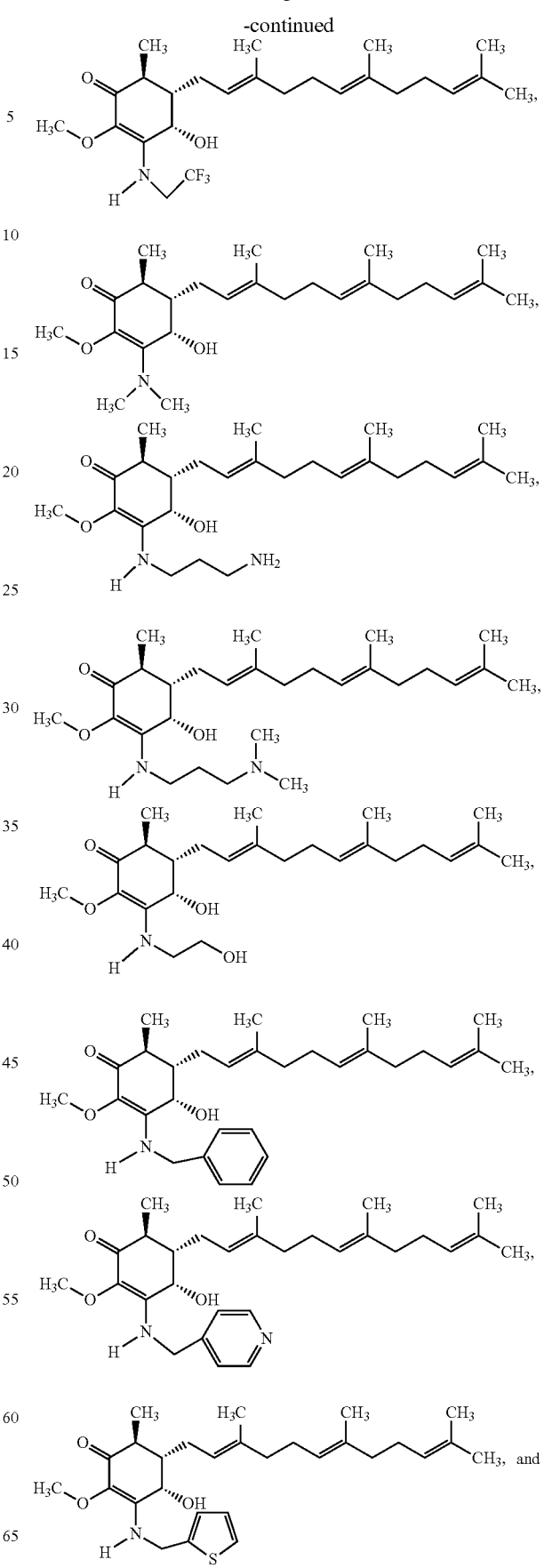

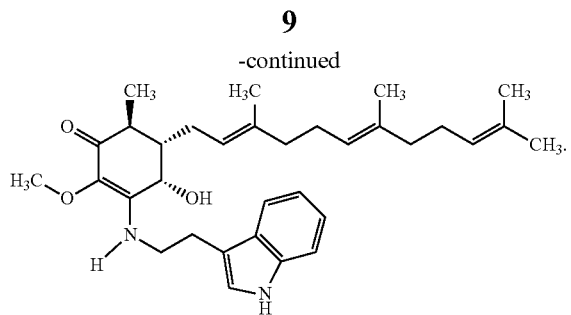
In certain embodiments, the compound is selected from the group consisting of
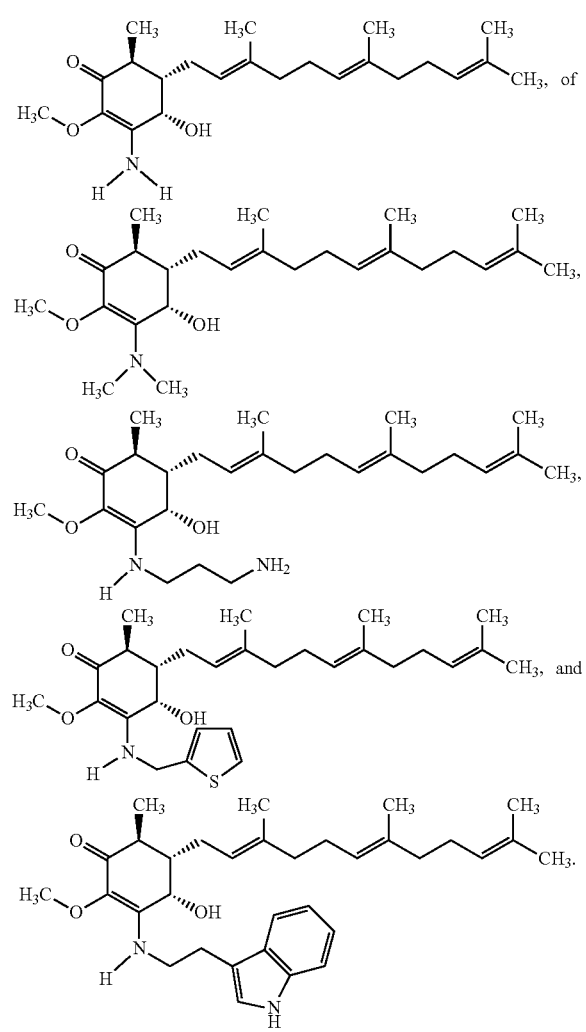
The following are some non-limited examples of invention compounds useful for anticancer treatments:
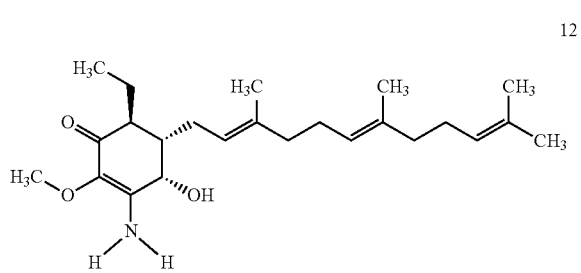
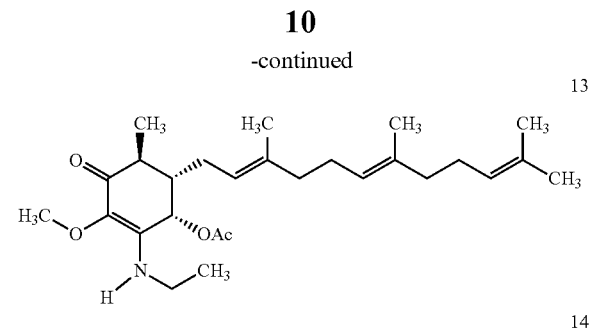
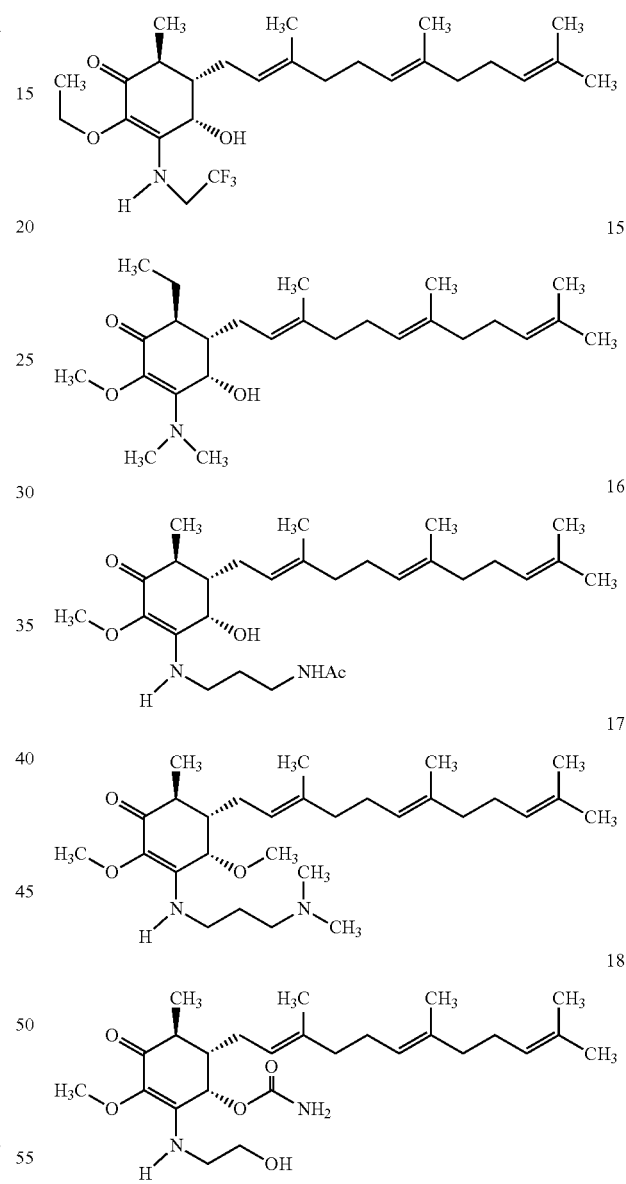

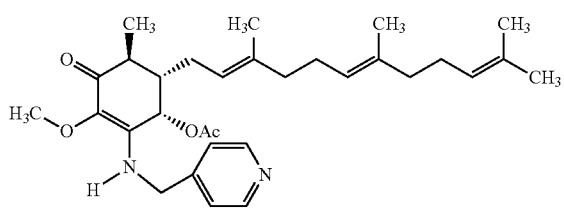

20

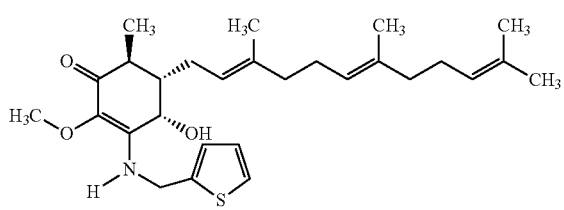

21

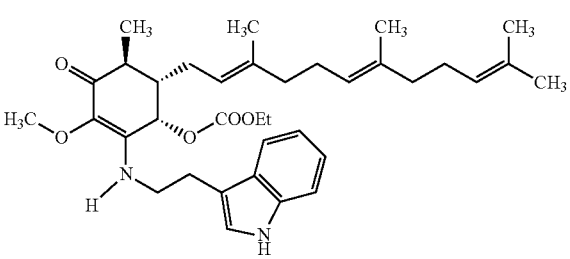

22

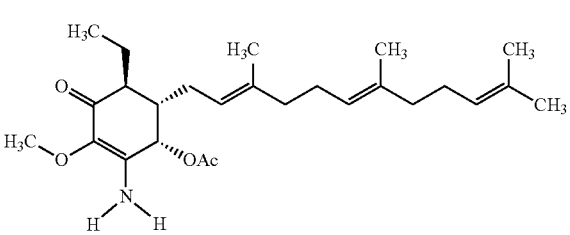

23

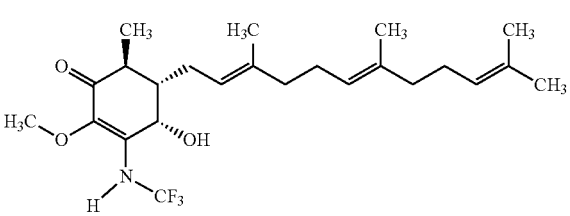

24

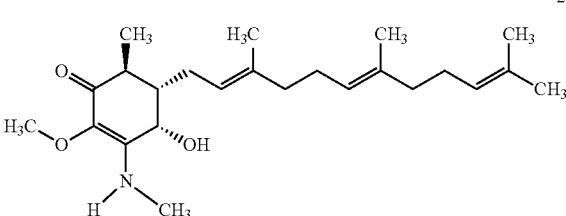

25

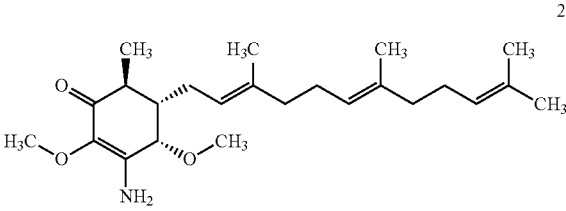

27

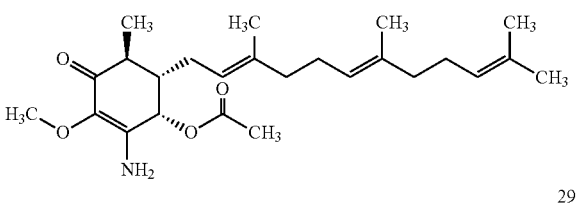

28

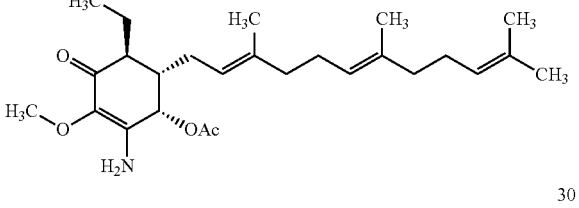

29

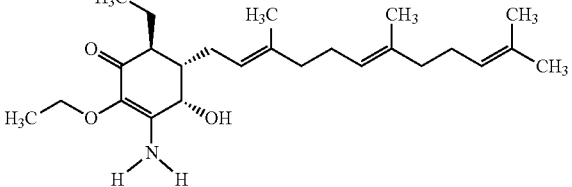

30

In some embodiments, the compounds disclosed herein are useful for treating or reducing the risk of liver cancer in a subject, especially in view of their unexpected benefit in inhibition of liver cancer cells in comparison with their respective 3-hydroxyl analogs.

In accordance with the present invention, there are provided methods for treating or reducing the risk of liver cancer in a subject comprising administering to said subject a therapeutically effective amount of an anti-cancer agent having the structure:

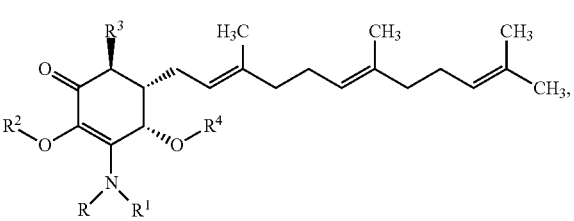

(I)

or a pharmaceutically acceptable salt, metabolite, solvate or prodrug thereof, wherein each of each of R, and $R^1$ independently is a hydrogen, $C(=O)OR_5$, $C(=O)R_5$, $C(=O)NR_5R_6$, or $C_1$-$C_8$ alkyl optionally substituted with one or more halogen, $NR_5R_6$, $OR_5$, aryl or heteroaryl;

each of $R^2$, and $R^3$ independently is a hydrogen, optionally substituted methyl or $(CH_2)_m$—$CH_3$, $R_4$ is H, $C(=O)OR_5$, $C(=O)R_5$, $C(=O)NR_5R_6$, $C_1$-$C_8$alkyl, $C_2$-$C_8$alkenyl, $C_2$-$C_8$alkynyl, wherein the $C_1$-$C_8$alkyl, $C_2$-$C_8$alkenyl, $C_2$-$C_8$alkynyl, are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently H or $C_1$-$C_8$alkyl;

$R_7$ is a $C_1$-$C_8$alkyl, $OR_5$ or $NR_5R_6$.

In certain embodiments, R is hydrogen (H), $C_1$-$C_8$alkyl, or $C_1$-$C_8$alkyl substituted with one or more halogen, $NR_5R_6$, $OR_5$, $C_6$-$C_{10}$aryl or $C_4$-$C_{10}$heteroaryl. In certain embodiments, R is a hydrogen (H), methyl, ethyl, propyl, butyl, pentyl, hexyl, or the like, optionally substituted with one or more halogen, $NR_5R_6$, $OR_5$, $C_6$-$C_{10}$aryl or $C_4$-$C_{10}$heteroaryl. In certain embodiments, R is H, or $C_1$-$C_8$alkyl. In certain embodiments, R is hydrogen, methyl, ethyl, propyl, butyl, pentyl, or hexyl. In certain embodiments, R is a hydrogen, C(=O)$OR_5$, C(=O)$R_5$, or C(=O)$NR_5R_6$. In certain embodiments, R is H, $C_1$-$C_8$alkyl, C(=O)$OR_5$, C(=O)$R_5$, or C(=O)$NR_5R_6$. In certain embodiments, R is H, or C(=O)$R_5$. In certain embodiments, R is H, C(=O)$C_3H_8$, C(=O)$C_2H_5$, or C(=O)$CH_3$. In certain embodiments, R is H, $C_1$-$C_8$alkyl, or $C_1$-$C_8$alkyl substituted with one or more $NR_5R_6$, or $C_4$-$C_{10}$heteroaryl.

In certain embodiments, $R^1$ is hydrogen (H). In certain embodiments, $R^1$ is hydrogen, $C_1$-$C_8$alkyl, or $C_1$-$C_8$alkyl substituted with one or more halogen, $NR_5R_6$, $OR_5$, $C_6$-$C_{10}$aryl or $C_4$-$C_{10}$heteroaryl. In certain embodiments, $C_6$-$C_{10}$aryl is phenyl. In certain embodiments, $C_4$-$C_{10}$heteroaryl is pyridyl, thiophenyl, or indolyl. In certain embodiments, $R^1$ is hydrogen, or $C_1$-$C_8$alkyl. In certain embodiments, $R^1$ is H, $C_1$-$C_8$alkyl, or $C_1$-$C_8$alkyl substituted with one or more $NR_5R_6$, or $C_4$-$C_{10}$heteroaryl. In certain embodiments, $R^1$ is a hydrogen (H), methyl, ethyl, propyl, butyl, pentyl, hexyl, or the like, optionally substituted with one or more halogen, $NR_5R_6$, $OR_5$, $C_6$-$C_{10}$aryl or $C_4$-$C_{10}$heteroaryl. In certain embodiments, $R^1$ is hydrogen, methyl, ethyl, propyl, butyl, optionally substituted with $NR_5R_6$, $OR_5$, $C_6$-$C_{10}$aryl or $C_4$-$C_{10}$heteroaryl. In certain embodiments, $R^1$ is hydrogen, methyl, methyl substituted with $C_4$-$C_{10}$heteroaryl such as thiophenyl, ethyl substituted with $OR_5$ such as OH, ethyl substituted with $C_4$-$C_{10}$heteroaryl such as indolyl, propyl substituted with $NR_5R_6$ such as $NH_2$. In certain embodiments, $R^1$ is hydrogen, methyl, methyl substituted with $C_4$-$C_{10}$heteroaryl such as thiophenyl, or propyl substituted with $NR_5R_6$ such as $NH_2$.

In some embodiments, R is hydrogen, or C(=O)$R_5$; and $R^1$ is hydrogen, $C_1$-$C_8$alkyl, or $C_1$-$C_8$alkyl substituted with one or more halogen, $NR_5R_6$, $OR_5$, $C_6$-$C_{10}$aryl or $C_4$-$C_{10}$heteroaryl. In certain embodiments, R is $C_1$-$C_8$alkyl and $R^1$ is $C_1$-$C_8$alkyl. In certain embodiments, R is hydrogen, and $R^1$ is hydrogen, $C_1$-$C_8$alkyl, or $C_1$-$C_8$alkyl substituted with one or more halogen, $NR_5R_6$, $OR_5$, $C_6$-$C_{10}$aryl or $C_4$-$C_{10}$heteroaryl. In particular, R is hydrogen, and $R^1$ is hydrogen, methyl, ethyl, propyl, butyl, optionally substituted with $NR_5R_6$, $OR_5$, $C_6$-$C_{10}$aryl or $C_4$-$C_{10}$heteroaryl. In certain embodiments, R is hydrogen, and $R^1$ is hydrogen, methyl, methyl substituted with $C_4$-$C_{10}$heteroaryl such as thiophenyl, ethyl substituted with $OR_5$ such as OH, ethyl substituted with $C_4$-$C_{10}$heteroaryl such as indolyl, or propyl substituted with $NR_5R_6$ such as $NH_2$. In certain embodiments, R is hydrogen or methyl, and $R^1$ is hydrogen, methyl, methyl substituted with $C_4$-$C_{10}$heteroaryl such as thiophenyl, or propyl substituted with $NR_5R_6$ such as $NH_2$.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless otherwise indicated, conventional methods of mass spectroscopy, NMR, HPLC, protein chemistry, biochemistry, recombinant DNA techniques and pharmacology are employed. Unless specific definitions are provided, the standard nomenclature employed in connection with, and the standard laboratory procedures and techniques of, analytical chemistry, synthetic organic chemistry, and medicinal and pharmaceutical chemistry are employed. In certain instances, standard techniques are used for chemical syntheses, chemical analyses, pharmaceutical preparation, formulation, and delivery, and treatment of patients. In certain embodiments, standard techniques are used for recombinant DNA, oligonucleotide synthesis, and tissue culture and transformation (e.g., electroporation, lipofection). In some embodiments, reactions and purification techniques are performed e.g., using kits of manufacturer's specifications or as commonly accomplished or as described herein.

As used throughout this application and the appended claims, the following terms have the following meanings:

The term "alkyl" as used herein, means a straight, branched chain, or cyclic (in this case, it would also be known as "cycloalkyl") hydrocarbon containing from 1-10 carbon atoms. Illustrative examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

The term "$C_1$-$C_a$alkyl" as used herein, means a straight, branched chain, or cyclic (in this case, it would also be known as "cycloalkyl") hydrocarbon containing from 1-8 carbon atoms. Representative examples of alkyl include, but are not limited to, methyl, ethyl, n-propyl, iso-propyl, cyclopyl, n-butyl, sec-butyl, tert-butyl, cyclobutyl, n-pentyl, isopentyl, neopentyl, cyclopentyl, and n-hexyl.

The term "halo" or "halogen" as used herein, means a —Cl, —Br, —I or —F.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). In one aspect, an arylene is a $C_6$-$C_{10}$ arylene. Exemplary arylenes include, but are not limited to, phenyl-1,2-ene, phenyl-1,3-ene, and phenyl-1,4-ene.

As used herein, the term "heteroaryl" or "$C_4$-$C_{10}$heteroaryl" employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen, and having 4 to 10 carbon atoms. In some embodiments, the heteroaryl group has 1, 2, 3, or 4 heteroatoms. In some embodiments, the heteroaryl group has 1, 2, or 3 heteroatoms. In some embodiments, the heteroaryl group has 1 or 2 heteroatoms. In some embodiments, the heteroaryl group has 1 heteroatom. When the heteroaryl group contains more than one heteroatom ring member, the heteroatoms may be the same or different. Example heteroaryl groups include, but are not limited to, pyrrolyl, azolyl, oxazolyl, thiazolyl, imidazolyl, furyl, thienyl, quinolinyl, isoquinolinyl, indolyl, benzothienyl, benzofuranyl, benzisoxazolyl, imidazo[1,2-b]thiazolyl or the like. In certain embodiments, the heteroaryl group has 5 to 10 carbon atoms.

The term "optionally substituted" or "substituted" means that the referenced group may be substituted with one or more additional group(s) indicated thereof. In some embodiments, if no additional group(s) indicated thereof, the group(s) may be individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. By way of example an optional substituents may be halide, —CN, —NO$_2$, or L$_s$R$_s$, wherein each L$_s$ is independently selected from a bond, —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$, —OC(=O)NH—, —NHC(=O)O—, or —(C$_1$-C$_6$ alkylene)-; and each R$_s$ is selected from H, alkyl, fluoroalkyl, heteroalkyl, cycloalkyl, aryl, heteroaryl, or heterocycloalkyl. The protecting groups that may form the protective derivatives of the above substituents may be found in sources such as Greene and Wuts, above. In some embodiments, optional substituents are selected from halogen, —CN, —NH$_2$, —OH, —N(CH$_3$)$_2$, alkyl, fluoroalkyl, heteroalkyl, cycloalkyl, heterocycloalkyl, aryl, heteroaryl, alkoxy, aryloxy, alkylthio, arylthio, alkylsulfoxide, arylsulfoxide, alkylsulfone, and arylsulfone. In some embodiments, an optional substituents is halogen, —CN, —NH$_2$, —OH, —NH(CH$_3$), —N(CH$_3$)$_2$, alkyl, fluoroalkyl, heteroalkyl, alkoxy, fluoroalkoxy, —S-alkyl, or —S(=O)$_2$ alkyl. In some embodiments, an optional substituent is selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, substituted groups are substituted with one of the preceding groups. In some embodiments, an optional substituent on an aliphatic carbon atom (acyclic or cyclic, saturated or unsaturated carbon atoms, excluding aromatic carbon atoms) includes oxo (=O).

The term "alkylene" refers to a divalent alkyl radical. Any of the above mentioned monovalent alkyl groups may be an alkylene by abstraction of a second hydrogen atom from the alkyl. In one aspect, an alkelene is a C$_1$-C$_6$alkylene. In another aspect, an alkylene is a C$_1$-C$_4$alkylene. Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

The term "alkenyl" refers to an unsaturated aliphatic group having at least one carbon-carbon double bond. In some embodiments, C$_2$-C$_8$alkenyl has at least two carbons and up to 8 carbons in said unsaturated aliphatic group.

The term "alkynyl" refers to an unsaturated aliphatic group having at least one carbon-carbon triple bond. In some embodiments, C$_2$-C$_8$alkynyl has at least two carbons and up to 8 carbons in said unsaturated aliphatic group.

EXAMPLE

Example 1: Preparation of Exemplary Amine Derivative Anticancer Agents

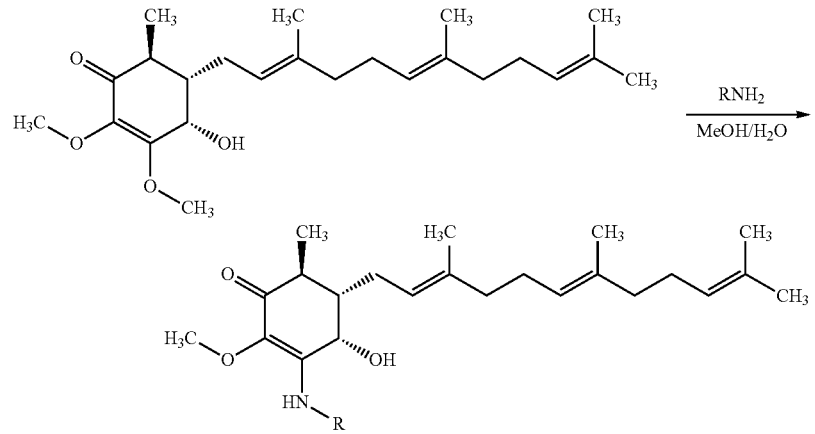

Scheme 1. Preparation of Amine Derivative Anti-Cancer Agent from 4-hydroxy-2,3-dimethoxy-6-methyl-5-(3,7,11-trimethyldodeca-2,6,10-trienyl)cyclohex-2-enone Exemplary anticancer agents were prepared according to Scheme 1 from 4-hydroxy-2,3-dimethoxy-6-methyl-5-(3,7,11-trimethyldodeca-2,6,10-trienyl)cyclohex-2-enone (100 mg, 0256 mmol) with a suitable amine reagent. A more detailed experimental procedure for preparation of Compound 1 is provided below.

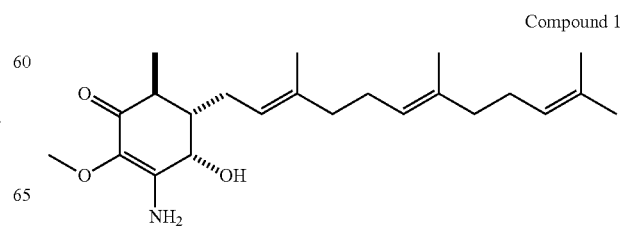

Compound 1

Compound 1: (4S,5S,6S)-3-amino-4-hydroxy-2-methoxy-6-methyl-5-((2E,6E)-3,7,11-trimethyldodeca-2,6,10-trien-1-yl)cyclohex-2-enone A 30% of ammonium hydroxide (NH$_4$OH) solution (2.6 mL, 66.8 mmol) was added to a solution of 4-hydroxy-2,3-dimethoxy-6-methyl-5-(3,7,11-trimethyldodeca-2,6,10-trienyl)cyclohex-2-enone (100 mg, 0.256 mmol) in MeOH (26 mL) under N$_2$ at ice bath. The mixture was stirred at room temperature under N$_2$ for 16 h. The excess ammonium hydroxide was removed, and the residue was extracted with CH$_2$Cl$_2$ (10 mL×3). The combined organic phases was washed with brine 10 mL, dried over Na$_2$SO$_4$, and concentrated in vacuo to get product 64 mg (0.17 mmol, 67%). $^1$H (600 MHz; CDCl$_3$) δ 1.14 (3H, d, J=7.4 Hz), 1.54 (3H, s), 1.54-1.56 (br, 6H), 1.63 (3H, s), 1.89-1.98 (5H, m), 1.98-2.07 (5H, m), 2.31-2.38 (1H, m), 2.39-2.46 (1H, m), 3.59 (3H, s), 4.72 (1H, d, J=4.4 Hz), 5.02-5.06 (2H, m), 5.10 (1H, t, J=7.3 Hz); $^{13}$C (125 MHz; CDCl$_3$) δ 15.9, 16.0, 16.1, 17.6, 25.6, 26.0, 26.5, 26.7, 39.6, 39.8, 42.0, 46.0, 59.0, 66.0, 122.0, 123.9, 124.3, 128.9, 131.2, 135.1, 137.8, 154.8, 192.0; EI-MS, m/z 398 [M+Na]$^+$.

Compounds 2 to 11 were prepared similarly and confirmed with analytical methods. The reagents and conditions are listed below in Table 1 for the preparation of Compounds 1-11.

TABLE 1

Preparation of Compounds 1-11 with 3-amino derivatives.

| Compound No. | RNH$_2$ | Temp. (° C.) | MS Result | Yield (%) |
|---|---|---|---|---|
| 1 | NH$_4$OH | rt | [M + Na]$^+$ 398 | 67 |
| 2 | 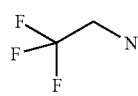 | rt | [M + H]$^+$ 404.19 [M + Na]$^+$ 426.13 | >95 |
| 3 | 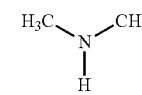 | 150 in sealed tube | [[M + Na]$^+$ 480.25 | 12 |
| 4 | 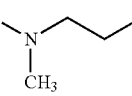 | rt | [M + H]$^+$ 404.13 [M + Na]$^+$ 426.13 | 45 |
| 5 | 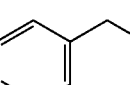 | rt | [M + H]$^+$ 433.28 [M + Na]$^+$ 455.17 | >95 |
| 6 | 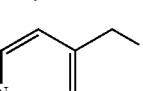 | rt | [M + H]$^+$ 461.25 [M + Na]$^+$ 483.32 | 99 |
| 7 | 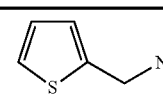 | rt | [M + Na]$^+$ 442.12 | 47 |
| 8 | 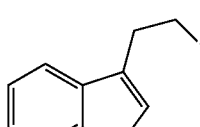 | rt | [M + Na]$^+$ 488.15 | 43 |
| 9 | 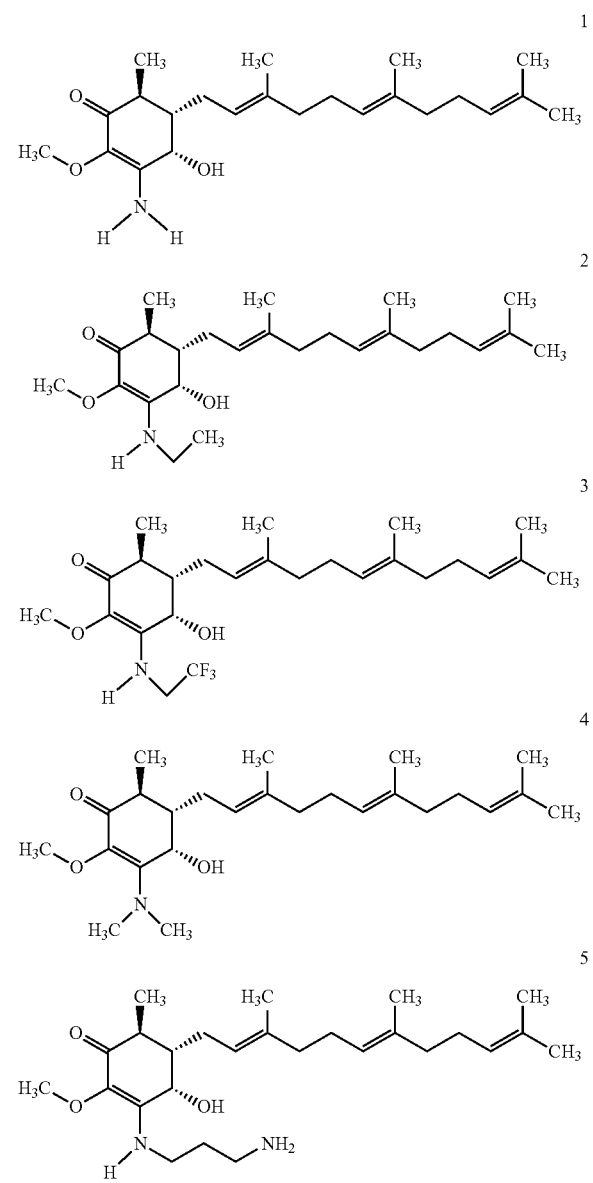 | 150 in sealed tube | [M + Na]$^+$ 489.09 | 52 |
| 10 | | 150 in sealed tube | [M + Na]$^+$ 494.17 | 83 |
| 11 | | rt | [M + Na]$^+$ 541.14 | 83 |

The following non exclusive exemplary compounds are prepared accordingly.

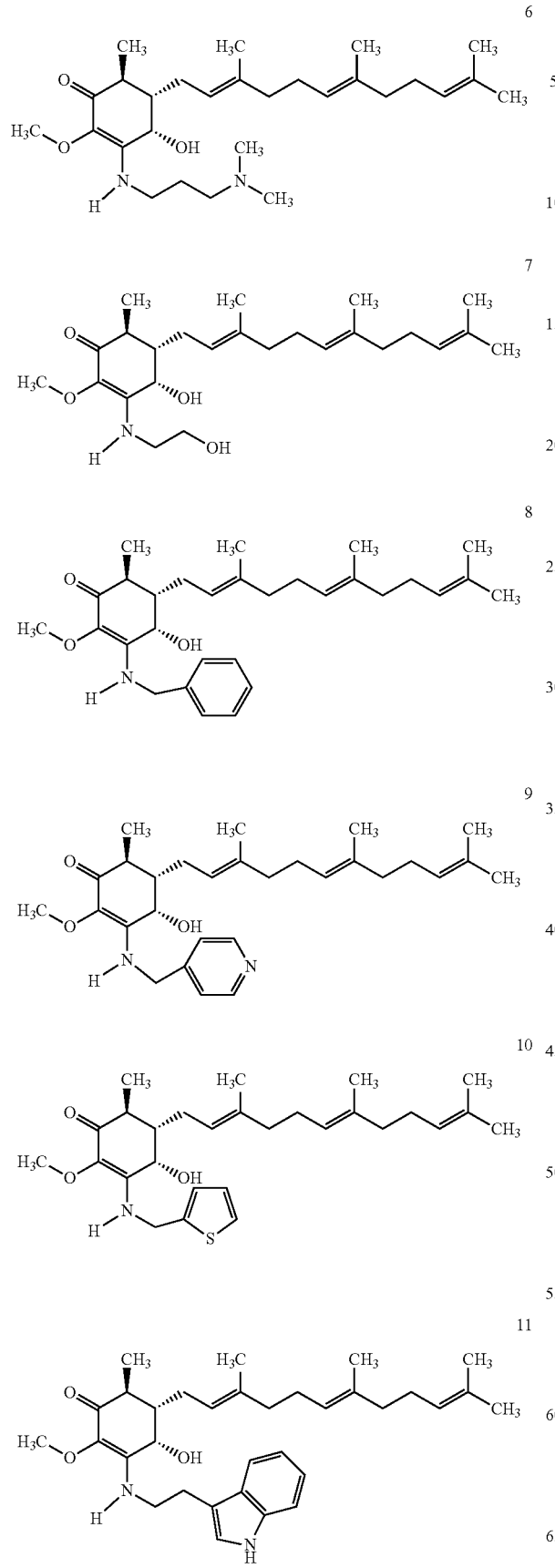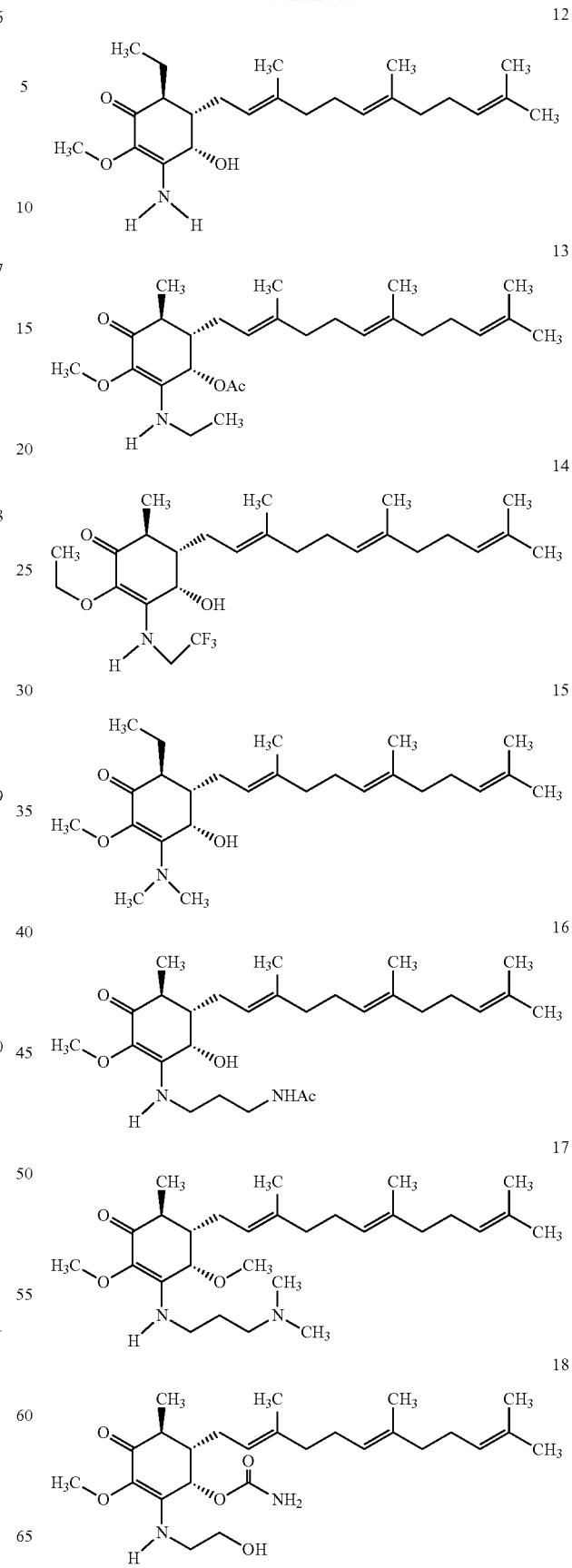

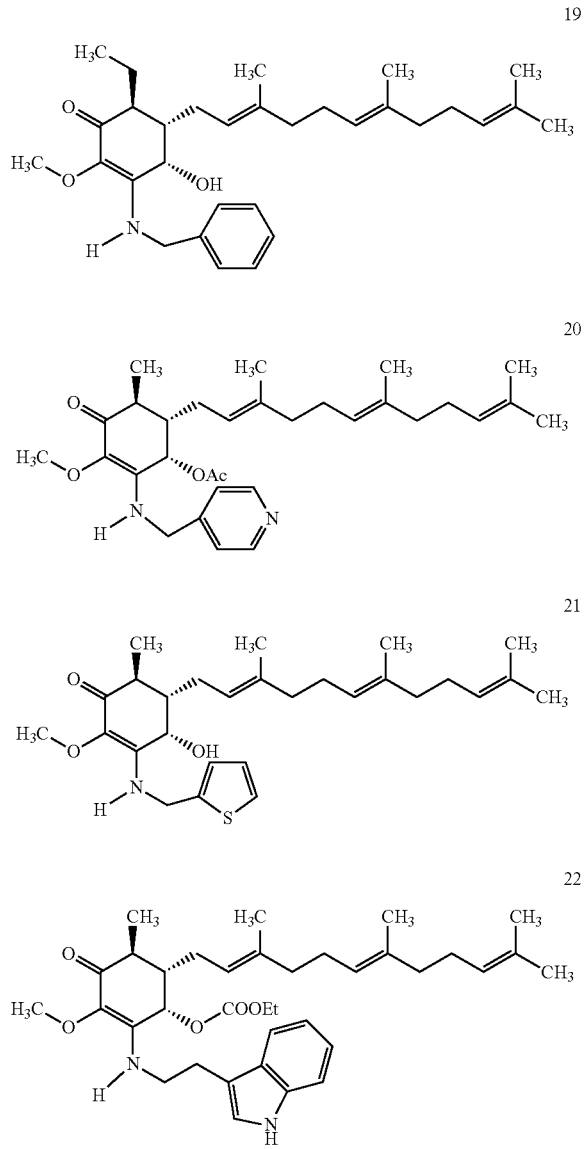

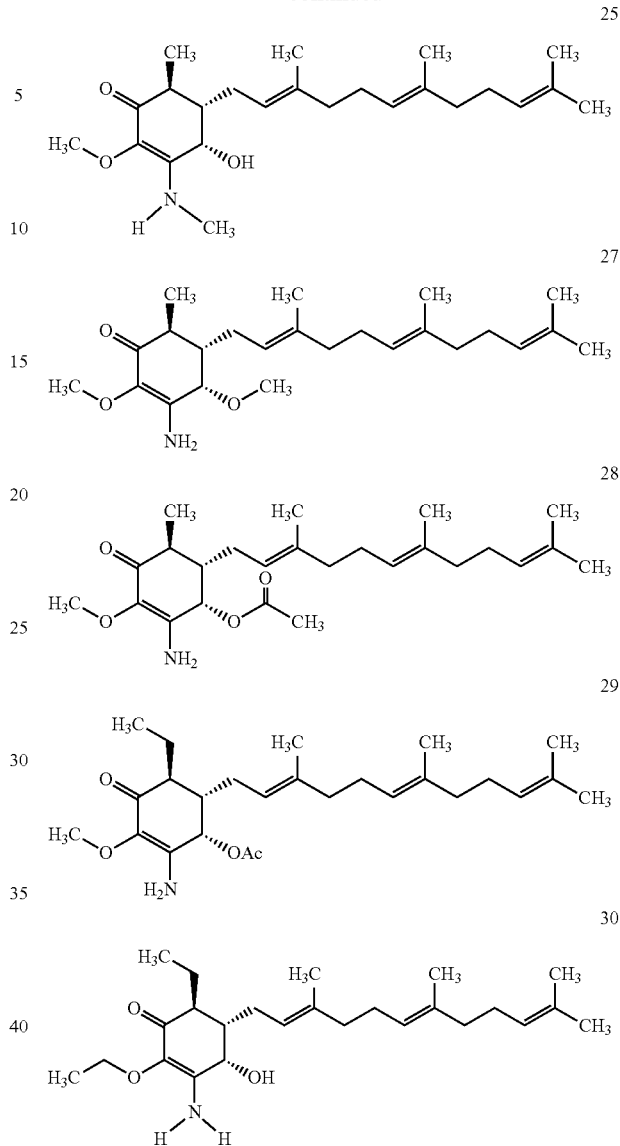

Example 2: MTT Assay

The MTT (3-(4, 5-dimethylthiazol-2-yl)-2,5-diphenyl tetrazolium bromide) cell viability assay is a colorimetric assay system, which measures the reduction of a tetrazolium component (MTT) into an insoluble blue/purple colored formazan product by succinate tetrazolium reductase in mitochondria of viable cells. The absorbance of the complex is read spectrophotometrically and is directly proportional to the number of live or viable cells. Formazan formation can therefore be used to assess and determine the survival rate of cells.

Human hepatoma cell lines (HepG2) were obtained from American Type Culture Collection (Rockville, Md., USA) and cultured in Minimum Essential Medium Alpha (Invitrogen/Gibco BRL, Grand Island, N.Y., USA) at 37° C. in 5% $CO_2$ in culture media supplemented with 10% fetal bovine serum (FBS) (Invitrogen/Gibco BRL) and 100 U/ml streptomycin and penicillin (Invitrogen/Gibco BRL).

100 μL of HepG2 cells ($1 \times 10^4$ cells per well) were seeded in 96 well plates and pre-incubated. After 24 h, the cells

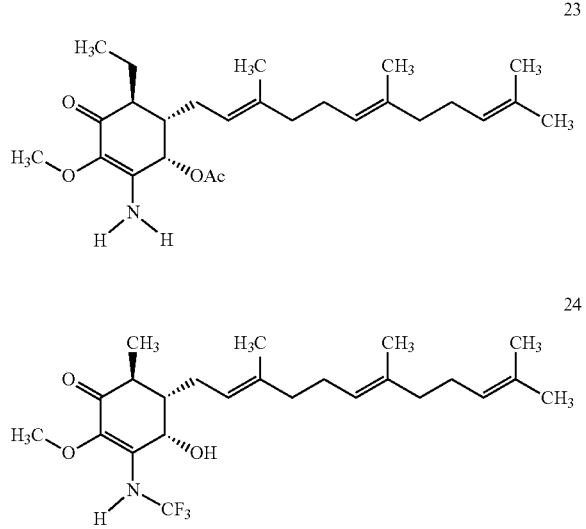

were exposed to various concentrations of Compounds 1-11, and the known compound 4-hydroxy-2,3-dimethoxy-6-methyl-5-(3,7,11-trimethyldodeca-2,6,10-trienyl)cyclohex-2-enone (Compound S) in a volume of 200 μL for 48 h. 20 μL of MTT reagent (5 mg/mL) was added to each well and then incubated in 5% $CO_2$ at 37° C. for 4 h. The media was replaced with 200 μL of DMSO to dissolve the MTT tetrazolium crystal. Absorbance was measured at 570 nm using a microplate reader. The results are shown in Table 2.

TABLE 2

MTT Assay Results

| Compound No. | $IC_{50}$ (ug/ml) |
| --- | --- |
| 1 | 0.13 |
| 2 | — |
| 3 | — |
| 4 | 0.18 |
| 5 | 0.87 |
| 6 | — |
| 7 | 1.95 |
| 8 | — |
| 9 | — |
| 10 | 0.91 |
| 11 | 2.29 |
| S | 2.4 |

The data clearly shows the exemplary amine derivatized anticancer agents exhibit unexpectedly better inhibition compared to 4-hydroxy-2,3-dimethoxy-6-methyl-5-(3,7,11-trimethyldodeca-2,6,10-trienyl)cyclohex-2-enone against liver cancer cells with some of them 10 to 20 folds better. In particular, Compounds 1, 4, 5, and 10 exhibit much better unexpected inhibition against liver cancer cells. With the major difference between Example 3: Efficacy Test of Exemplary Compound 1 on Liver Cancer Xenograft Model Thymic nude mice (National Laboratory Animal Center) of four to six weeks old were used and maintained in laminar flow cabinets under pathogen-free condition. Human HCC Mahlavu cells (1×10⁶ cells) carrying luciferase gene were re-suspended in 20 μL of PBS containing 50% matrigel (BD Biosciences, MA) and injected into the left lateral liver lobe of athymic nude mice (National Laboratory Animal Center) with 27-gauge needle by sterile techniques (Lu et al., 2007). For bioluminescence imaging, the animals were injected with the luciferase substrate D-luciferin at a dose of 150 mg/kg in 0.2 mL sterile isotonic saline.

Tumor growth and metastatic status was monitored using the Xenogen International Veterinary Information Service (IVIS) imaging system every two weeks. All images were obtained after intraperitoneal injection of luciferin (100 mg/kg body weight; Synchem, Elk Grove Village, Ill., United States). Ten minutes after injection of luciferin, nude mice were placed onto the Xenogen IVIS imaging stage and were continuously sedated during image acquisition. Image analysis and bioluminescence quantification were performed using Living Image software (Caliper Life Sciences, Hopkinton, Mass., United States). BLI is based on the detection of light emitted by living cells expressing a luciferase gene. The tumor-bearing mice were treated with vehicle (olive oil) or Compound 1 at 120 mg/kg by oral gavage twice per day and 5 days per week for 4 weeks. The body weight was measured twice weekly.

Results

FIG. 1 shows decrease of the tumor size of THP-1 xenograft mice treated with the exemplary test compound. The tumor-bearing mice were treated with vehicle (olive oil) or Compound 1 at 120 mg/kg by oral gavage twice per day and 5 days per week for 4 weeks. The tumor volume was measured twice weekly. ***P<0.005 compared to vehicle control.

Figure 2:
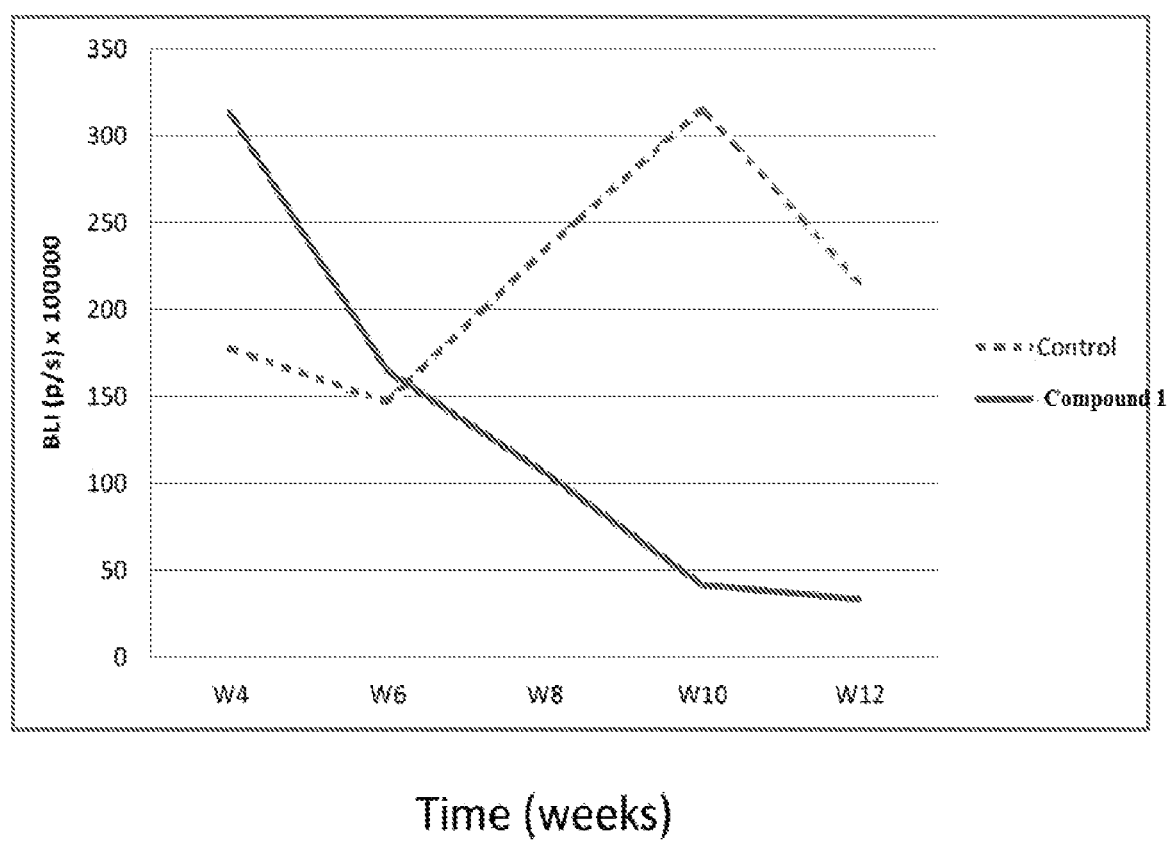
FIG. 2 illustrates the tumor mass test results by weight of THP-1 xenograft mice treated with and without with the exemplary invention compound.

FIG. 2 shows the decrease tumor mass weight at the end point of THP-1 xenograft mice treated with test compound. At the end of week 12, tumor mass of the mice treated with Compound 1 decrease at least 4 folds compared with one without treatment (the control).

Figure 3:
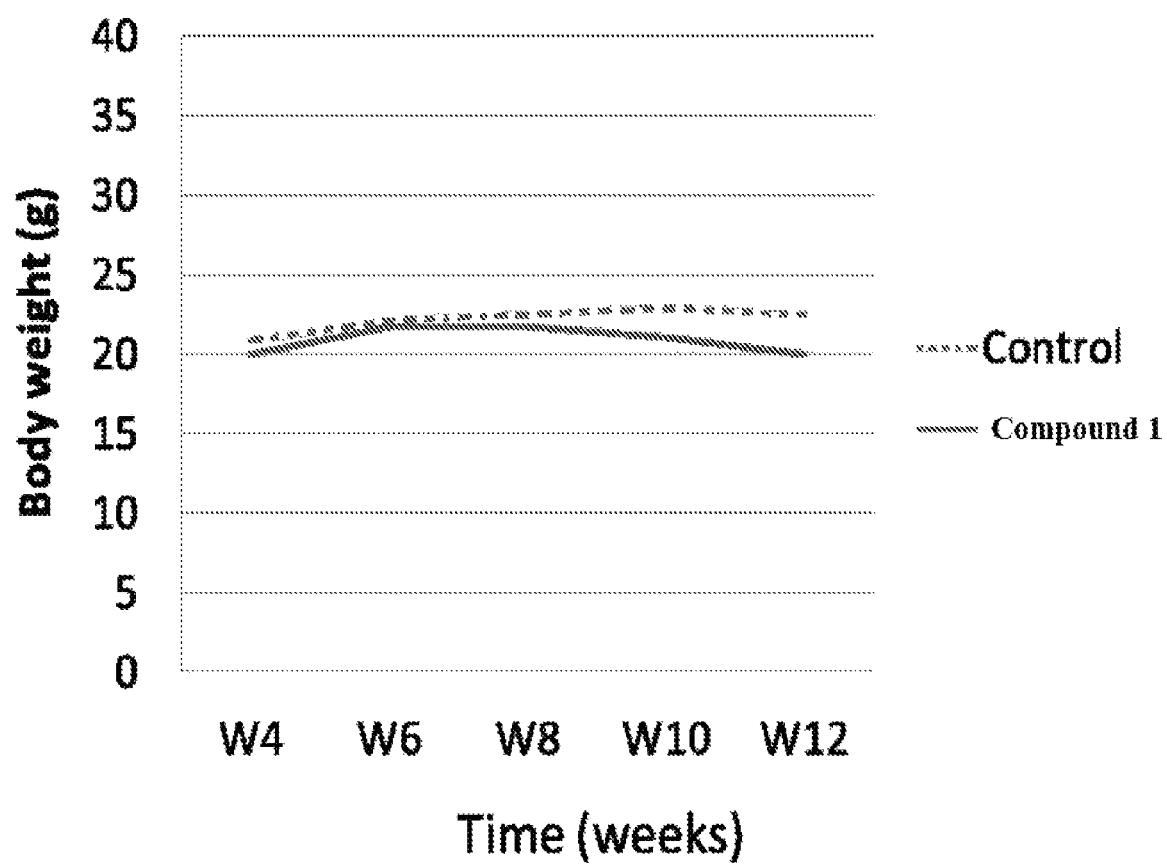
FIG. 3 illustrates the body weight test results of THP-1 xenograft mice treated with and without the exemplary invention compound.

FIG. 3 shows the results of body weight changes of THP-1 xenograft mice treated with or without test compound. The almost no change of body weight indicates the test compound did not cause any serious side effects.

These results clearly demonstrate the effectness and efficacy exemplary invention Compound 1 on liver cancer treatment based on xenograft model.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound of formula I:

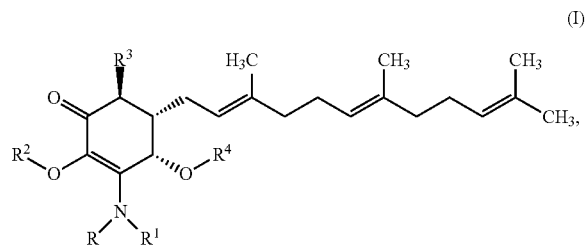

(I)

or a pharmaceutically acceptable salt, metabolite, or solvate thereof, wherein each of R, and $R^1$ independently is a hydrogen, $C(=O)OR_5$, $C(=O)R_5$, $C(=O)NR_5R_6$, or $C_1$-$C_8$alkyl optionally substituted with one or more halogen, $NR_5R_6$, $OR_5$, aryl or heteroaryl;

$R^2$ is a hydrogen, $C(=O)OR_5$, $C(=O)R_5$, $C(=O)NR_5R_6$, or $C_1$-$C_8$alkyl optionally substituted with one or more halogen, aryl or heteroaryl, $R^3$ is a hydrogen, optionally substituted methyl or $(CH_2)_m$—$CH_3$, m=0-6, $R^4$ is H, $C(=O)OR_5$, $C(=O)R_5$, $C(=O)NR_5R_6$, $C_1$-$C_8$alkyl, $C_2$-$C_8$alkenyl, $C_2$-$C_8$alkynyl, wherein the $C_1$-$C_8$alkyl, $C_2$-$C_8$alkenyl, $C_2$-$C_8$alkynyl, are optionally substituted with one or more substituents selected from $NR_5R_6$, $OR_5$, $OC(=O)R_7$, $C(=O)OR_5$, $C(=O)R_5$, $C(=O)NR_5R_6$, $C_1$-$C_8$ alkyl, $C_2$-$C_8$ alkenyl, $C_2$-$C_8$ alkynyl, $C_3$-$C_8$ cycloalkyl, and $C_1$-$C_8$ haloalkyl;

each of $R_5$ and $R_6$ is independently H or $C_1$-$C_8$alkyl; $R_7$ is a $C_1$-$C_8$alkyl, $OR_5$ or $NR_5R_6$.

2. The compound of claim 1, wherein $R^3$ is a methyl and $R^4$ is H.

3. The compound of claim 1, wherein $R^3$ is hydrogen, methyl, ethyl, propyl, butyl, pentyl, hexyl.

4. The compound of claim 1, wherein $R^4$ is H methyl, ethyl, propyl, butyl, pentyl, hexyl, C(=O)OR$_5$, C(=O)R$_5$, or C(=O)NR$_5$R$_6$.

5. The compound of claim 1, wherein each of R, and $R^1$ independently is a hydrogen, methyl, ethyl, propyl, butyl, pentyl, hexyl optionally substituted with one or more halogen, NR$_5$R$_6$, OR$_5$, aryl or heteroaryl.

6. The compound of claim 5, wherein $R^1$ is a hydrogen, methyl, ethyl, propyl, butyl, pentyl, hexyl optionally substituted with one or more halogen, NR$_5$R$_6$, or heteroaryl.

7. The compound of claim 1, wherein R is hydrogen, or $C_1$-$C_8$alkyl.

8. The compound of claim 1, R is hydrogen, C(=O)OR$_5$, C(=O)R$_5$, or C(=O)NR$_5$R$_6$.

9. The compound of claim 1, wherein $R^1$ is hydrogen, or $C_1$-$C_8$alkyl optionally substituted with one or more halogen, NR$_5$R$_6$, OR$_5$, aryl or heteroaryl, and R is H, or C(=O)R$_5$.

10. The compound of claim 9, wherein $R^2$ is methyl, ethyl, propyl, butyl, pentyl, hexyl.

11. The compound of claim 9, wherein $R^2$ is C(=O)OR$_5$, C(=O)R$_5$, C(=O)NR$_5$R$_6$.

12. The compound of claim 1, wherein said compound is selected from the group consisting of

-continued

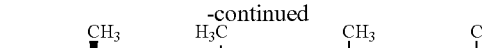

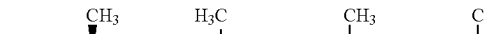

13. The compound of claim 1, wherein said compound is selected from the group consisting of

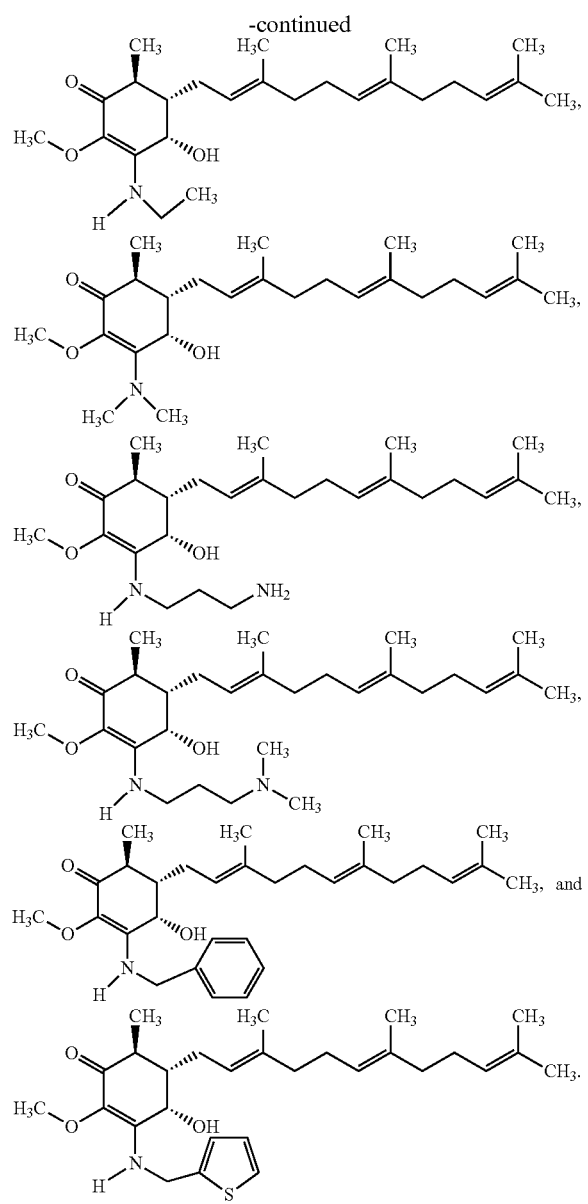

14. A method for treating liver cancer in a subject comprising administering to the subject an effective amount of a compound of claim 1.

15. The method of claim 14, wherein said compound inhibits liver cancer cells.

16. The method of claim 14, wherein said compound decreases cancer tumor mass weight.

17. The method of claim 14, wherein said compound reduces cancer tumor size.

18. The method of claim 14, wherein said compound is selected from the group consisting of

* * * * *